United States Patent
Brendel

(10) Patent No.: US 9,978,158 B2
(45) Date of Patent: *May 22, 2018

(54) SPECTRAL PROJECTION DATA DE-NOISING WITH ANTI-CORRELATION FILTER

(71) Applicant: KONINKLIJKE PHILIPS N.V., Eindhoven (NL)

(72) Inventor: Bernhard Johannes Brendel, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/912,106

(22) PCT Filed: Aug. 29, 2014

(86) PCT No.: PCT/IB2014/064137
§ 371 (c)(1),
(2) Date: Feb. 15, 2016

(87) PCT Pub. No.: WO2015/028975
PCT Pub. Date: Mar. 5, 2015

(65) Prior Publication Data
US 2016/0180554 A1 Jun. 23, 2016

Related U.S. Application Data

(60) Provisional application No. 61/871,952, filed on Aug. 30, 2013.

(51) Int. Cl.
*G06T 11/00* (2006.01)
*A61B 6/00* (2006.01)
*A61B 5/00* (2006.01)

(52) U.S. Cl.
CPC .......... *G06T 11/005* (2013.01); *A61B 5/0071* (2013.01); *A61B 5/0073* (2013.01);
(Continued)

(58) Field of Classification Search
CPC .... G06T 11/005; G06T 11/006; G06T 11/008; A61B 5/00071; A61B 5/0073; A61B 6/5205; A61B 6/5211
See application file for complete search history.

(56) References Cited

U.S. PATENT DOCUMENTS

| | | | |
|---|---|---|---|
| 4,897,788 A | | 1/1990 | King et al. |
| 5,953,444 A | * | 9/1999 | Joseph .......... G06T 11/005 378/7 |

(Continued)

FOREIGN PATENT DOCUMENTS

WO    2012095713    7/2012

OTHER PUBLICATIONS

Wonseok Huh, et al, "Iterative Image Reconstruction for Dual-Energy X-Ray CT Using Regularized Material Sinogram Estimates", 2011 8th IEEE International Symposium on Biomedical Imaging: From Nano to Macro (ISBI 2011), Mar. 30, 2011.

(Continued)

*Primary Examiner* — Manav Seth

(57) ABSTRACT

A method includes receiving at least two sets of noisy basis material line integrals, each set corresponding to a different basis material and filtering the at least two sets of noisy basis material line integrals with an anti-correlation filter that at least includes a regularization term with balancing regularization factors, thereby producing de-noised basis material line integrals. An imaging system (100) includes a projection data processor (116) with an anti-correlation filter (118) that filters at least two sets of noisy basis material line integrals, each set corresponding to a different basis mate- (Continued)

rial, thereby producing de-noised basis material line integrals, wherein the anti-correlation filter includes a regularization term with regularization balancing factors.

20 Claims, 4 Drawing Sheets

(52) U.S. Cl.
CPC ........ *A61B 6/5205* (2013.01); *G06T 2210/41* (2013.01); *G06T 2211/408* (2013.01); *G06T 2211/424* (2013.01)

(56) References Cited

U.S. PATENT DOCUMENTS

| | | | | |
|---|---|---|---|---|
| 6,507,633 B1* | 1/2003 | Elbakri | ................ | G06T 11/006 378/4 |
| 6,754,298 B2* | 6/2004 | Fessler | ................ | A61B 6/032 378/15 |
| 7,940,884 B2* | 5/2011 | Bruder | ................ | G06T 11/006 378/4 |
| 8,538,114 B2* | 9/2013 | Yang | ................ | G06T 5/002 382/131 |
| 8,565,854 B2* | 10/2013 | Bryskhe | ................ | A61B 5/055 324/307 |
| 8,600,137 B2* | 12/2013 | Bruder | ................ | A61B 6/032 382/131 |
| 8,705,831 B2* | 4/2014 | Koehler | ................ | G06T 5/50 382/131 |
| 8,718,343 B2* | 5/2014 | Bruder | ................ | A61B 6/032 382/131 |
| 8,750,588 B2* | 6/2014 | Bruder | ................ | A61B 6/032 382/131 |
| 8,965,144 B2* | 2/2015 | Yang | ................ | G06T 5/002 382/275 |
| 8,989,469 B2* | 3/2015 | Fahimian | ................ | A61B 6/032 378/19 |
| 9,600,866 B2* | 3/2017 | Brendel | ................ | G06T 5/002 |
| 2003/0156684 A1* | 8/2003 | Fessler | ................ | A61B 6/032 378/210 |
| 2013/0121555 A1* | 5/2013 | Bruder | ................ | G06T 11/003 382/131 |
| 2014/0005971 A1* | 1/2014 | Roessl | ................ | G06T 11/005 702/104 |

OTHER PUBLICATIONS

Baojun Li, et al, "Simultaneous Reduction in Noise and Cross-Contamination Artifacts for Dual-Energy X-Ray CT", Biomed Research International, vol. 174, No. 1, Jun. 19, 2013.

Richard Warp, et al., "Quantitative Evaluation of Noise Reduction Strategies in Dual-Energy Imaging", Medical Physics, AIP, vol. 30, No. 2, Feb. 1, 2003.

* cited by examiner

SPECTRAL PROJECTION DATA DE-NOISING WITH ANTI-CORRELATION FILTER

CROSS REFERENCE TO RELATED APPLICATIONS

This application is the U.S. National Phase application under 35 U.S.C. § 371 of International Application No. PCT/IB2014/064137, filed Aug. 29, 2014, published as WO 2015/028975 on Mar. 5, 2015, which claims the benefit of U.S. Provisional Patent Application No. 61/871,952 filed Aug. 30, 2013. These applications are hereby incorporated by reference herein.

The following generally relates to projection data processing and more particularly to projection domain de-noising of projection data with an anti-correlation filter that includes a regularization term with sub-terms for each basis material and corresponding scaling factors, and is described with particular application to spectral (i.e., multi-energy) computed tomography (CT). However, the following is also amenable to other imaging modalities.

A CT scanner includes an x-ray tube that emits radiation that traverses an examination region and an object therein. A detector array located opposite the examination region across from the x-ray tube detects radiation that traverses the examination region and the object therein and generates projection data indicative of the examination region and the object therein. A reconstructor processes the projection data and reconstructs volumetric image data indicative of the examination region and the object therein.

With a spectral CT scanner, multiple projection data sets are acquired, which represent the attenuation properties of the scanned object for different X-ray spectra. The multiple sets can be acquired through kVp switching, dual layer detectors, counting detectors, and/or otherwise. Based on these data sets, physical object properties can be determined locally (e.g., photo effect, Compton scattering, water content, bone content, iodine content, etc.). The determination of these properties is called material decomposition.

With projection domain processing, the material decomposition is performed by converting the measured line integrals for each ray into basis material line integrals. The basis material line integrals are then reconstructed to generate basis material images. However, the noise of the measured projection data tends to be strongly magnified, and the magnified noise is highly anti-correlated for the different material line integrals of one acquisition ray.

The anti-correlated noise can lead to streak artifacts, and images directly reconstructed from the basis material line integrals tend to be very noisy due to the noise amplification, reducing their clinical value. An anti-correlation filter (ACF) can be used to filter the anti-correlated noise. Unfortunately, the application of an ACF to the basis material line integrals may lead to crosstalk between the basis material data sets, producing artifacts that reduce the diagnostic value of the reconstructed basis material images.

Aspects described herein address the above-referenced problems and others.

This application describes an approach in which anti-correlated noise in spectral basis material line integrals is reduced through an anti-correlation filter that includes a regularization term with sub-terms for each basis material and corresponding scaling factors, wherein the scaling factors balance the effect of each sub-term, mitigating crosswalk between tissue boundaries, which may be present without such balancing.

In one aspect, a method includes receiving at least two sets of noisy basis material line integrals, each set corresponding to a different basis material and filtering the at least two sets of noisy basis material line integrals with an anti-correlation filter that at least includes a regularization term with balancing regularization factors, thereby producing de-noised basis material line integrals.

In another aspect, an imaging system includes a projection data processor with an anti-correlation filter. The anti-correlation filter filters at least two sets of noisy basis material line integrals, each set corresponding to a different basis material, thereby producing de-noised basis material line integrals. The anti-correlation filter includes a regularization term with regularization balancing factors, In another aspect, computer readable instructions are encoded on computer readable storage medium, which, when executed by a processor of a computing system, cause the processor to: receive at least two sets of noisy basis material line integrals, each set corresponding to a different basis material and filter the at least two sets of noisy basis material line integrals with an anti-correlation filter that at least includes a regularization term with balancing regularization factors, thereby producing de-noised basis material line integrals.

The invention may take form in various components and arrangements of components, and in various steps and arrangements of steps. The drawings are only for purposes of illustrating the preferred embodiments and are not to be construed as limiting the invention.

FIG. 1 schematically illustrates a projection data processor with an anti-correlation filter in connection with an imaging system.

FIG. 2 schematically illustrates a non-limiting example of the anti-correlation filter, which is based on a regularized maximum likelihood algorithm with regularization sub-term balancing scaling factors.

Figure 1:
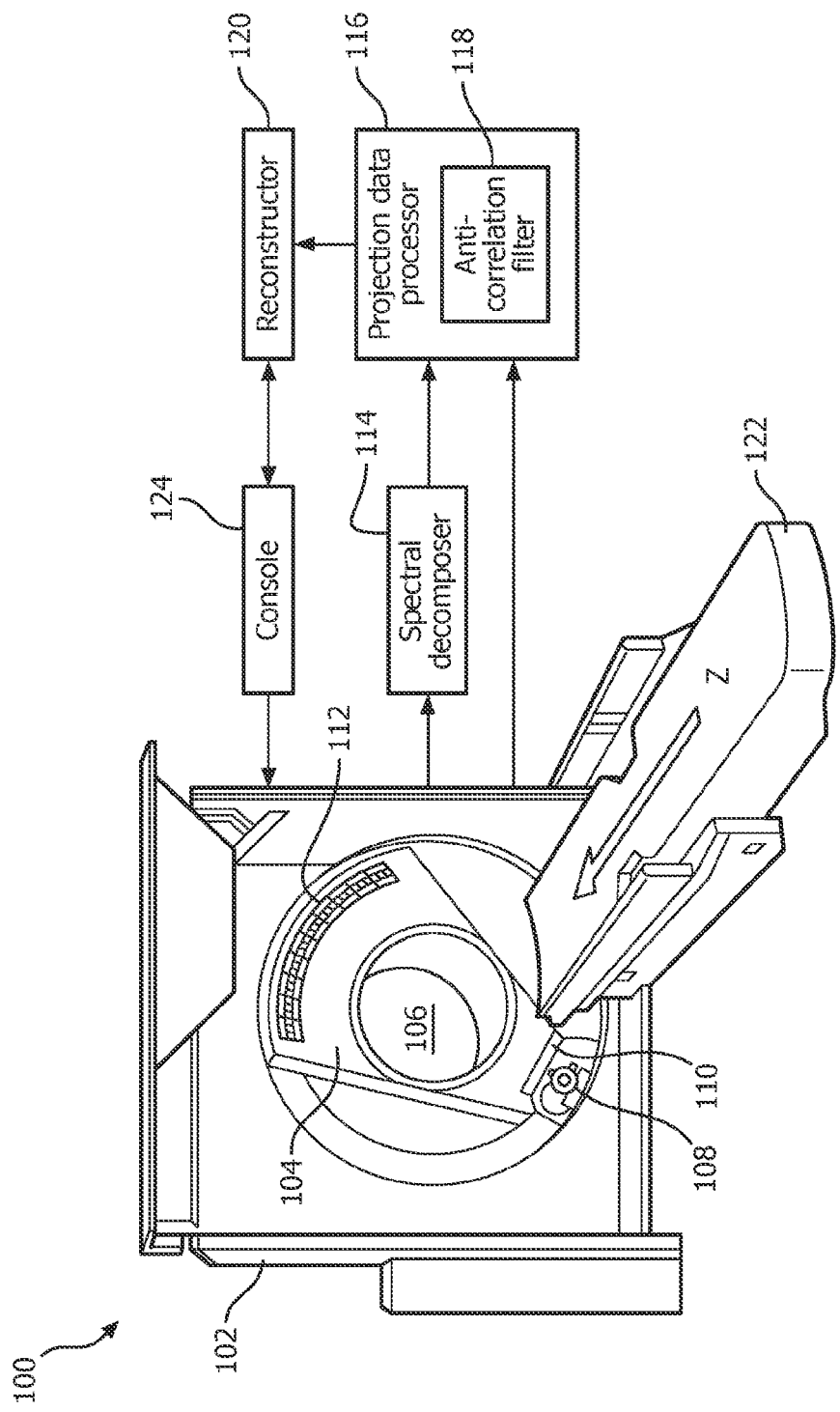

Initially referring to FIG. 1, an imaging system 100, such as a computed tomography (CT) scanner, is schematically illustrated. The imaging system 100 includes a generally stationary gantry 102 and a rotating gantry 104. The rotating gantry 104 is rotatably supported by the stationary gantry 102 and rotates around an examination region 106 about a longitudinal or z-axis.

A radiation source 108, such as an x-ray tube, is rotatably supported by the rotating gantry 104. The radiation source 108 rotates with the rotating gantry 104 and emits radiation that traverses the examination region 106. A source collimator 110 includes collimation members that collimate the radiation to form a generally cone, wedge, fan or other shaped radiation beam.

A radiation sensitive detector array 112 subtends an angular arc opposite the radiation source 108 across the examination region 106. The detector array 112 includes one or more rows of detectors that extend along the z-axis direction. The detector array 112 detects radiation traversing the examination region 106 and generates projection data (or measured line integrals) indicative thereof.

In the illustrated embodiment, the projection data is spectral projection data and includes at least two sub-sets of projection data, each representing attenuation properties of the scanned object for different X-ray spectra. Such projection data can be obtained where the detector array 112 includes a photon counting detector and/or a multi-layer spectral detector, and/or the radiation source 108 is configured to switch between at least two different energy spectrums during a scan.

A spectral decomposer 114 decomposes the spectral projection data generated by the radiation sensitive detector array 112, producing decomposed spectral projection data, or basis material line integrals. The decomposition can be based on two or more basis materials such as the photoelectric effect, Compton scattering, water content, bone content, iodine content, a k-edge, and/or other basis material(s).

A projection data processor 116 processes the decomposed spectral projection data. The illustrated projection data processor 116 includes at least an anti-correlation filter (ACF) 118. The ACF 118 at least filters anti-correlated noise from the decomposed spectral projection data. This includes filtering the anti-correlated noise using an iterative statistical model. An example of a suitable anti-correlation filter 118 includes a regularized maximum likelihood filter that includes a data term and a regularization term. As described in greater detail below, the regularization term includes two or more sub-terms, one for each basis material, and corresponding balancing scaling factors, which mitigate crosstalk at the tissue-air boundaries.

A reconstructor 120 reconstructs the de-noised decomposed projection data and generates volumetric image data indicative thereof, including material basis volumetric image data. A patient support 122, such as a couch, supports an object or subject such as a human patient in the examination region 106. A computing system or computer serves as an operator console 124, which allows an operator to control an operation of the system 100, such as selecting and/or activating at least a projection domain de-noising algorithm.

In the illustrated embodiment, the projection data processor 116 is a separate device with respect to the console 124. In this instance, the projection data processor 116 can be part of a computing system such as a dedicated computer and/or other computing system. In a variation, the projection data processor 116 is part of the console 124. In either instance, the projection data processor 116 can be implemented via a processor (e.g., a microprocessor, a central processing unit or CPU, or the like) executing computer readable instructions stored on computer readable storage medium such as physical memory (and excluding non-transitory medium). The processor can also execute instructions carried by a carrier wave, signal or other transitory medium.

Figure 2:
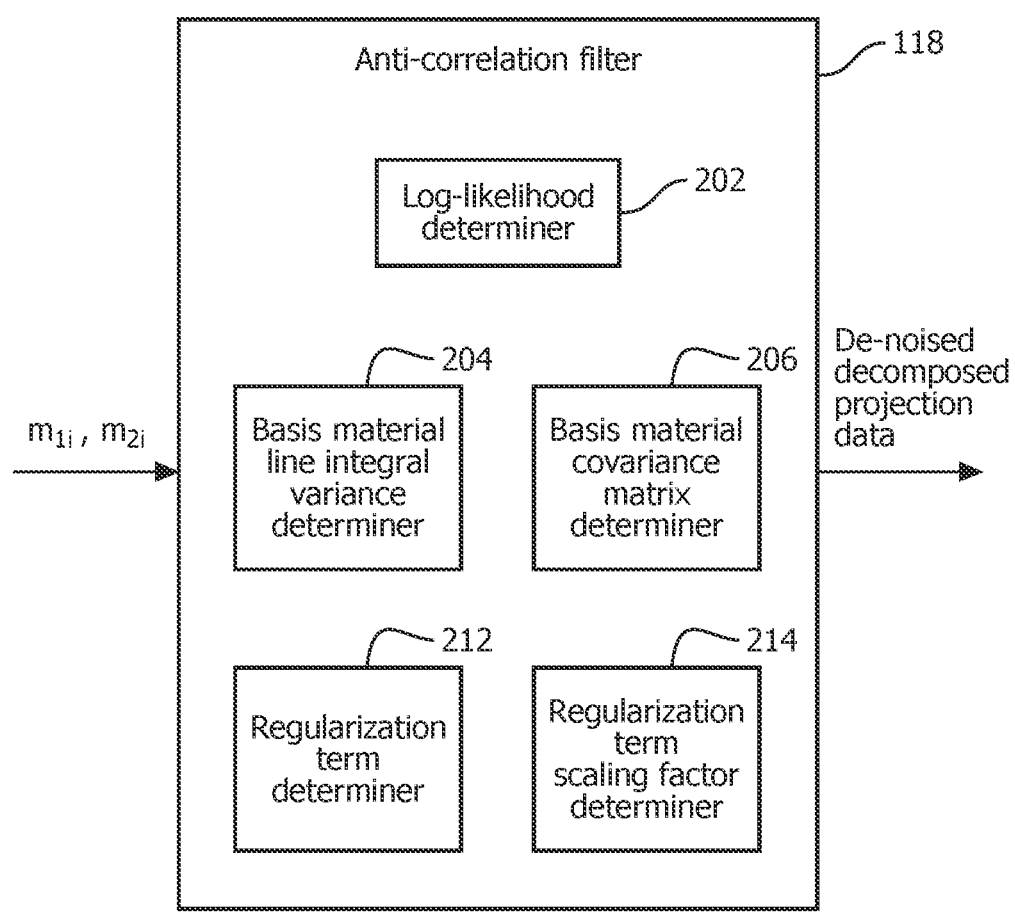

FIG. 2 illustrates a non-limiting example of the anti-correlation filter 118.

For sake of brevity and clarity, the following is discussed in connection with two sub-sets of spectral projection data. However, it is to be understood that the following can be extended to more than two sub-sets of spectra projection data.

The anti-correlation filter 118 receives, as input, the decomposed or basis material line integrals $m_{1i}$ and $m_{2i}$, where i is an acquired ray index, and outputs de-noised decomposed projection data (basis material line integrals).

A log likelihood determiner 202 processes data based on a regularized maximum likelihood algorithm, generating the de-noised decomposed projection data. An example of a suitable regularized maximum likelihood is shown in EQUATION 1:

$$\hat{L} \equiv -\frac{1}{2}\sum_i (m_i - \overline{m}_i)^T C_i^{-1}(m_i - \overline{m}_i) - \beta \sum_i \sqrt{R_{1i}^2 + R_{2i}^2}, \quad \text{EQUATION 1}$$

where $m_i = (m_{1i}, m_{2i})$ and represents a vector of the two sets of noisy basis material line integrals, $\overline{m}_i = (\overline{m}_{1i}, \overline{m}_{2i})$ and represents a vector of the two sets of de-noised basis material line integrals, $C_i$ represent the covariance matrices describing the correlated noise in $m_{1i}$ and $m_{2i}$, $R_{1i}$ and $R_{2i}$ represent basis material regularization sub-terms for two material sinograms, and $\beta$ is a parameters that determines of strength of the regularization.

Other regularization terms are also contemplated herein. For instance, application Ser. No. 61/729,782, filed Nov. 26, 2012, and entitled "PROJECTION DATA DE-NOISING," which is incorporated by references herein in its entirety, describes suitable regularization terms.

In EQUATION 1, the first term is a data term, describing the probability that the de-noised material line integrals belong to the noisy material line integrals given known variances and covariances. The second term is a regularization term that represents a-priori information about the "true" set of material line integrals. EQUATION 1 is implemented by an iterative optimization until the de-noised material line integrals that most probably belong to the noisy material line integrals are identified.

A basis material line integral variance determiner 204 processes the received basis material line integrals $m_{1i}$ and $m_{2i}$ and generates basis material line integral variances $var(m_{1i})$ and $var(m_{2i})$ and covariances $cov(m_{1i}, m_{2i})$.

A basis material covariance matrix determiner 206 determines the covariance matrix $C_i$, based on the basis material line integral variances $var(m_{1i})$ and $var(m_{2i})$ and the basis material line integral covariances $cov(m_{1i}, m_{2i})$. For example, the covariance matrix $C_i$ can be determined as shown in EQUATION 2:

$$C_i = \begin{pmatrix} var(m_{1i}) & cov(m_{1i}, m_{2i}) \\ cov(m_{1i}, m_{2i}) & var(m_{2i}) \end{pmatrix}. \quad \text{EQUATION 2}$$

The regularization terms $R_{1i}$ and $R_{2i}$ can be determined as shown in EQUATIONS 3 and 4:

$$R_{1i} = \sum_k w_{ik} \psi(\overline{m}_{1i} - \overline{m}_{1k}), \quad \text{EQUATION 3}$$

$$R_{2i} = \sum_k w_{ik} \psi(\overline{m}_{2i} - \overline{m}_{2k}). \quad \text{EQUATION 4}$$

In these EQUATIONS, the priors are smoothed with a potential function $\psi$. The potential function evaluates, for each measured ray i, the difference of the material line integral value to the values of a number of neighboring rays k, where $w_{ik}$ are weighting factors.

Due to the regularization terms $R_{1i}$ and $R_{2i}$ the optimization of EQUATION 1 will lead to a pair of de-noised material line integral sets which are, in sum, optimally smooth. Due to the strong anti-correlation between the two material line integral data sets $m_{1i}$ and $m_{2i}$ the optimization will on the other hand (due to the data term) compensate, e.g., a reduction of one material line integral value $m_{1i}$ by an increase of the corresponding value $m_{2i}$.

This will lead, especially at edges, to crosstalk between the two materials. For example, at a boundary between air and soft tissue, there will be an edge between low values (air) and high values (tissue) in both sinograms. Due to the regularization, the optimization tends to smooth both edges, and due to the data term, it is not possible to smooth both edges, since this leads to a reduction or increase of both corresponding values $m_{1i}$ and $m_{2i}$.

If the regularization term and the data term are not correctly balanced, the result will be a smoothing of the edge in one material data set and an enhancement of the same edge in the other material data set, such that, in sum, the regularization terms have a more optimal value as compared to do no smoothing at the edge. This is an unwanted behavior leading to image artifacts, which reduce the clinical value of the images.

EQUATIONS 5 and 6 show regularization terms $R_{1i}$ and $R_{2i}$ that are respectively balanced via scaling terms $f_{1i}$ and $f_{2i}$ such that any attempt by the regularization terms to smooth both edges is not influenced by an attempt of the data term to allow only changes that are in accordance with the anti-correlation of both material data sets:

$$R_{1i} = f_{1i} \sum_k w_{ik} \psi(\overline{m}_{1i} - \overline{m}_{1k}), \quad \text{EQUATION 5}$$

$$R_{2i} = f_{2i} \sum_k w_{ik} \psi(\overline{m}_{2i} - \overline{m}_{2k}). \quad \text{EQUATION 6}$$

The scaling terms $f_{1i}$ and $f_{2i}$ balance the regularization terms $R_{1i}$ and $R_{2i}$ such that crosstalk at tissue-air boundaries is reduced, relative to the regularization terms $R_{1i}$ and $R_{2i}$ of EQUATIONS 3 and 4. This is illustrated in FIGS. 3 and 4.

Figure 3:
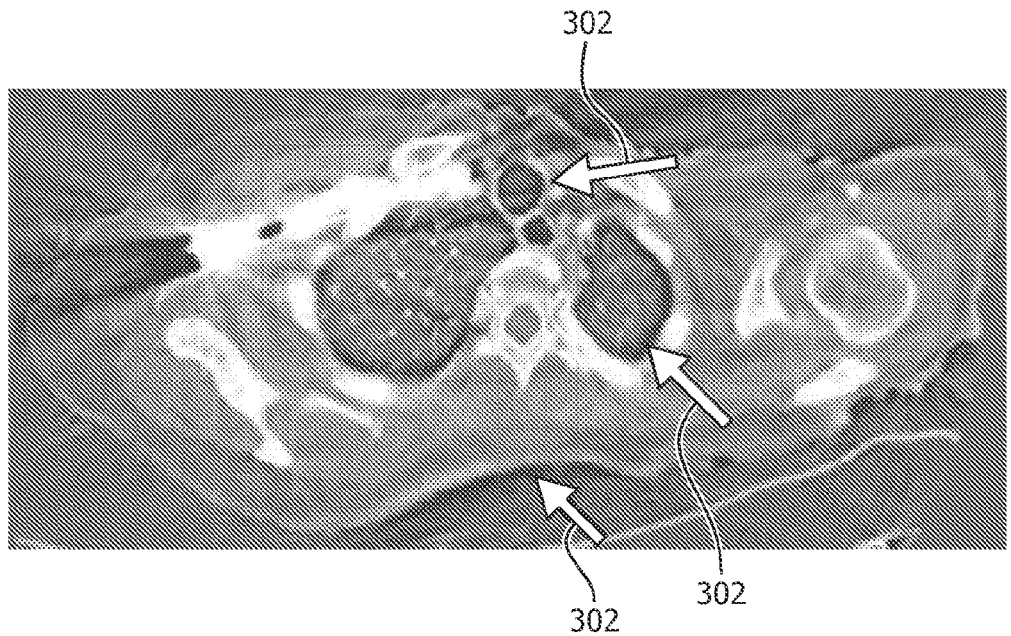
FIG. 3 shows an example image generated with an anti-correlation filter with no regularization sub-term balancing.
Figure 4:
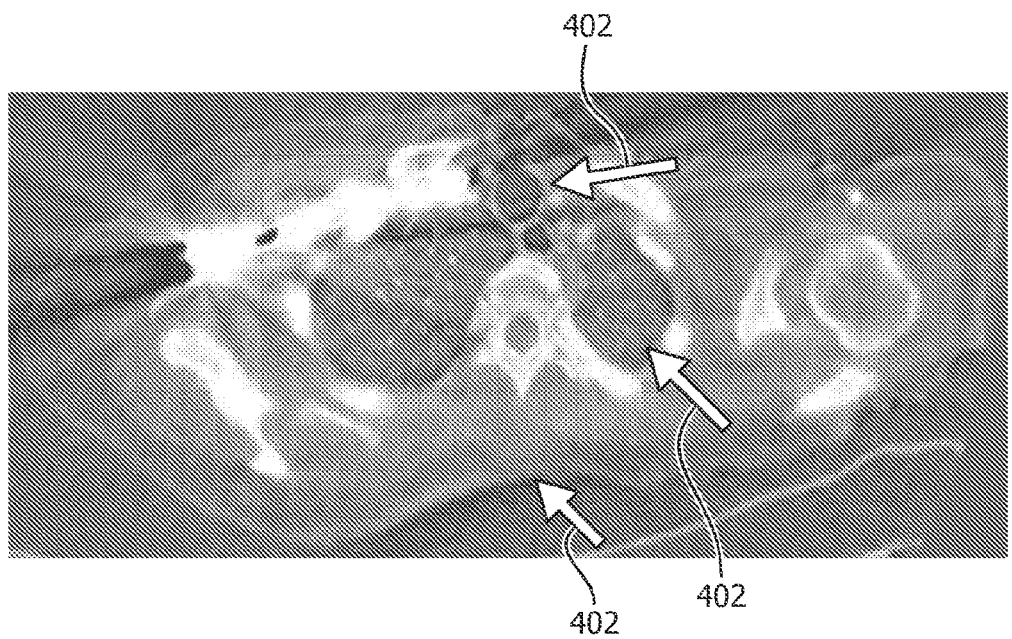
FIG. 4 shows an example image generated with the anti-correlation filter described herein, which includes regularization sub-term balancing.

FIG. 3 shows an example image generated from projection data filtered with a regularized anti-correlation filter without sub-term balancing (e.g., EQUATIONS 3 and 4). Regions 302 identify artificial dark regions at the boundaries of the lungs, the trachea and the body. FIG. 4 shows an example image generated from projection data processed with EQUATION 1, using the regularization sub-terms of EQUATIONS 5 and 6 with balancing. The artifacts in FIG. 4 are reduced in regions 402 relative to the artifacts in the regions 302 of FIG. 3.

Generally, $f_{1i}$ and $f_{2i}$ are determined such that they satisfy predetermined criteria. For example, in one instance, suitable criteria includes $f_{1i}/f_{2i}$=a predetermined constant. The following describes a non-limiting example approach for determining $f_{1i}$ and $f_{2i}$.

At, e.g., the outer boundary of an object, the material line integral values $m_{1i}$ and $m_{2i}$ drop from finite values to zero for both materials. An aim of the regularization terms is to get both finite values closer to zero at the edge, leading to an intended change which is in line with the direction of the vector $(-m_{1i}, -m_{2i})$. An aim of the data term, on the other hand, is to allow only changes which are in accordance with the noise correlation between the two values $m_{1i}$ and $m_{2i}$. The direction of preferred changes is given by vector $(\text{sqrt}(\text{var}(m_{1i})), -\text{sqrt}(\text{var}(m_{2i})))$ if the correlation is close to $-1$.

If these two directions are not orthogonal, crosstalk will appear between the two materials. Thus, $m_{1i}$ and $m_{2i}$ are to be scaled such that the direction of change given by the regularization is orthogonal to $(\text{sqrt}(\text{var}(m_{1i})), -\text{sqrt}(\text{var}(m_{2i})))$. This can be achieved by scaling $m_{1i}$ with $f_{1i}=\text{sqrt}(m_{2i}*\text{sqrt}(\text{var}(m_{2i})))$ and $m_{2i}$ with $f_{2i}=\text{sqrt}(m_{1i}*\text{sqrt}(\text{var}(m_{1i})))$. Then, the change due to the regularization term will be in the direction of $(f_1*m_{1i}, f_2*m_{2i})$ and the change due to the data term will be in the direction of $(f_1*\text{sqrt}(\text{var}(m_{1i})), -f_2*\text{sqrt}(\text{var}(m_{2i})))$, which are orthogonal.

Other approaches for determining $f_{1i}$ and $f_{2i}$ are also contemplated herein.

Figure 5:
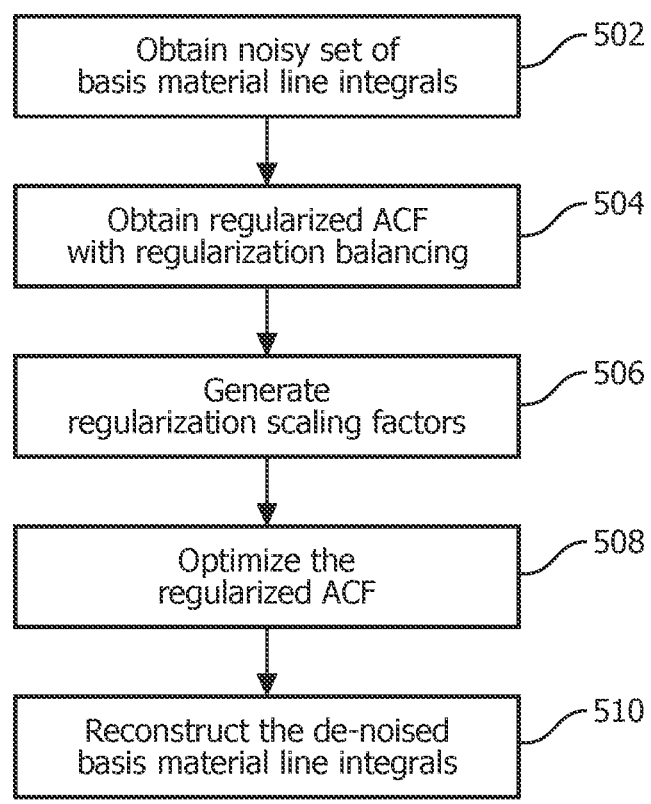
FIG. 5 illustrates an example method for de-noising projection data with an anti-correlation filter with a regularized maximum likelihood algorithm that includes regularization sub-term balancing scaling factors.

FIG. 5 illustrates an example method for de-noising projection data with an anti-correlation filter with regularization balancing.

It is to be appreciated that the ordering of the acts in the method described herein is not limiting. As such, other orderings are contemplated herein. In addition, one or more acts may be omitted and/or one or more additional acts may be included.

At 502, a set of noisy basis material line integrals from a spectral scan are obtained.

At 504, an anti-correlation filter with regularization balancing is obtained.

At 506, scaling factors for balancing regularization sub-terms are generated.

At 508, the regularized maximum likelihood algorithm is optimized, producing de-noised basis material line integrals.

Generally, this includes implementing an iterative optimization to identify de-noised basis material line integrals with a relatively highest probability of belonging to the noisy material line integrals.

At 510, the de-noised basis material line integrals are reconstructed, producing volumetric image data, including basis material volumetric image data.

The above methods may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   receiving at least two sets of noisy basis material line integrals, each set corresponding to a different basis material, wherein the at least two sets of noisy basis material line integrals are produced by a computed tomography scanner; and
   filtering the at least two sets of noisy basis material line integrals with an anti-correlation filter that at least includes a regularization term with balancing regularization factors, thereby producing de-noised basis material line integrals.

2. The method of claim 1, further comprising:
   reconstructing the de-noised decomposed basis material line integrals, thereby generating basis material volumetric image data.

3. The method of claim 1, wherein the anti-correlation filter is based on a statistical model.

4. The method of claim 3, wherein the statistical model includes an iterative regularized maximum likelihood algorithm.

5. The method of claim 4, wherein the regularized maximum likelihood algorithm includes a data term and the regularization term, which includes a sub-term for each of the basis materials.

6. The method of claim 5, further comprising:
determining a regularization factor for each of the basis materials.

7. The method of claim 5, wherein a ratio of one regularization factor to another regularization factor equals a predetermined constant value.

8. The method of claim 6, further comprising:
determining a first regularization factor as a square root of a product of a first set of the noisy basis material line integrals for a first material and a standard deviation of the first set of noisy basis material line integrals; and
determining a second regularization factor as a square root of a product of a second set of noisy basis material line integrals for a second material and a standard deviation of the second set of noisy basis material line integrals.

9. The method of claim 8, wherein the regularization term includes a sum of square roots of a sum of squares of the sub-terms.

10. The method of claim 6, wherein the regularization factors cause the date term and the regularization term to change in directions that are orthogonal to each other.

11. An imaging system, comprising:
projection data processor, including:
an anti-correlation filter that is configured to filter at least two sets of noisy basis material line integrals, each set corresponding to a different basis material, thereby producing de-noised basis material line integrals, wherein the at least two sets of noisy basis material line integrals are produced by a computed tomography scanner, and wherein the anti-correlation filter includes a regularization term with regularization balancing factors.

12. The imaging system of claim 11, further comprising:
a reconstructor that processes the de-noised decomposed basis material line integrals, thereby generating basis material volumetric image data.

13. The imaging system of claim 11, wherein the regularization term includes a sub-term for each different basis material, and the anti-correlation filter, comprising:
a regularization term scaling factor determiner that determines a regularization term scaling factor for each of the sub-terms.

14. The imaging system of claim 13, wherein a ratio of one regularization scaling factor to another regularization scaling factor equals a predetermined constant value.

15. The imaging system of claim 13, wherein the regularization term scaling factor determiner determines a first regularization factor as a square root of a product of a first set of the noisy basis material line integrals for a first material and a standard deviation of the first set of noisy basis material line integrals, and determines a second regularization factor as a square root of a product of a second set of noisy basis material line integrals for a second material and a standard deviation of the second set of noisy basis material line integrals.

16. The imaging system of claim 13, wherein the regularization term includes a sum of square roots of a sum of squares of the sub-terms.

17. The imaging system of claim 11, the anti-correlation filter, further comprising:
a basis material integral variance determiner that determines variances of the noisy basis material line integrals;
a basis material integral covariance determiner that determines covariances between the noisy basis material line integrals;
wherein the anti-correlation filter determines the de-noised basis material line integrals based on the variances, covariance, and the regularization term.

18. The imaging system of claim 17, the anti-correlation filter, further comprising:
a log-likelihood determiner that identifies a set of de-noised material line integrals most likely belonging to the noisy material line integrals based on the variances, the covariances, and the regularization term, wherein the identified set of de-noised material line integrals are the produced de-noised basis material line integrals.

19. The imaging system of claim 18, wherein the log-likelihood determiner performs two or more iterations to identify the set of de-noised material line integrals.

20. Computer readable instructions encoded on a non-transitory computer readable storage medium, which, when executed by a processor of a computing system, causes the processor to:
receive at least two sets of noisy basis material line integrals, each set corresponding to a different basis material, wherein the at least two sets of noisy basis material line integrals are produced by a computed tomography scanner; and
filter the at least two sets of noisy basis material line integrals with an anti-correlation filter that at least includes a regularization term with balancing regularization factors, thereby producing de-noised basis material line integrals.

* * * * *